US007480049B2

(12) United States Patent
Manolopoulos et al.

(10) Patent No.: US 7,480,049 B2
(45) Date of Patent: Jan. 20, 2009

(54) CIRCULAR DICHROISM DETECTION SYSTEM

(75) Inventors: Spyros Manolopoulos, Warwick (GB); David Thomas Clarke, Appleton (GB); Peter David Read, Didcot (GB); Gareth Royston Jones, Bowdon (GB); Gareth Ernest Derbyshire, Harwell (GB)

(73) Assignee: The Science and Technology Facilities Council, Warrington (GB)

( * ) Notice: Subject to any disclaimer, the term of this patent is extended or adjusted under 35 U.S.C. 154(b) by 270 days.

(21) Appl. No.: 10/543,803

(22) PCT Filed: Jan. 30, 2004

(86) PCT No.: PCT/GB2004/000365

§ 371 (c)(1),
(2), (4) Date: Jul. 29, 2005

(87) PCT Pub. No.: WO2004/068119

PCT Pub. Date: Aug. 12, 2004

(65) Prior Publication Data

US 2006/0192959 A1 Aug. 31, 2006

(30) Foreign Application Priority Data

Feb. 1, 2003 (GB) .................................. 0302378.5

(51) Int. Cl.
*G01J 4/00* (2006.01)
(52) U.S. Cl. ..................................................... 356/364
(58) Field of Classification Search ....................... None
See application file for complete search history.

(56) References Cited

U.S. PATENT DOCUMENTS

| 5,018,856 | A | | 5/1991 | Harnly et al. |
| 5,521,706 | A | * | 5/1996 | Green et al. ................. 356/369 |
| 5,737,077 | A | | 4/1998 | Lee et al. |
| 5,920,393 | A | | 7/1999 | Kaplan |

FOREIGN PATENT DOCUMENTS

| EP | 0 916 945 A1 | 5/1999 |
| FR | 2 529 338 | 12/1983 |
| FR | A-2529338 | 12/1983 |

OTHER PUBLICATIONS

PEM-Based Vibrational Circular Dichroism, Hinds Instruments, Inc. PEM Applications News for Users of Photoelastic Modulators, Summer 1996 (pp. 1-4).

(Continued)

*Primary Examiner*—Hwa(Andrew) S Lee
(74) *Attorney, Agent, or Firm*—Bose McKinney & Evans LLP

(57) ABSTRACT

A detection system includes a modulator to apply a circular polarization modulation to an incident beam of radiation, a sample holder through which the modulated beam is pass, a grating to diffract the beam of radiation, an array of solid state detectors arranged to receive different wavelengths of the beam, and a process arranged to synchronise detected signals with the modulation applied by the modulator, in order to measure the spectral circular dichroism of the sample.

51 Claims, 4 Drawing Sheets

OTHER PUBLICATIONS

Schalike, et al., *An Instrument for measuring circular dichroism simultaneously at all wavelengths in a limited spectral range*, Rev. Sci. Instrum. 62 (8), Aug. 1991, © 1991 American Institute of Physics, pp. 1912-1915.

Hecht, et al., *Raman Optical Activity Instrument for Studies of Biopolymer Structure and Dynamics*, Journal of Raman Spectroscopy, Department of Chemistry, University of Glasgow, Glasgow G12 8QQ, UK, Copyright © 1999 John Wiley & Sons, Ltd., pp. 815-825.

Carrato S., et al., (1989) Versatile Low-Cost Digital Lock-In Amplifier Suitable for Multichannel Phase-Sensitive Detection, Rev. Sci. Instrum. 60: 2257-2259.

Probst Pierre-Alain, et al., (1994) Multiple-Channel Digital Lock-In Amplifier with PPM Resolution. Rev. Sci. Instrum. 65: 747-750.

European Patent Office Communication Pursuant to Article 94(3) EPC; Date: Jan. 28, 2008.

\* cited by examiner

CIRCULAR DICHROISM DETECTION SYSTEM

This application is the U.S. national phase under 35 U.S.C. § 371 of PCT International Application No. PCT/GB2004/000365, which has an International filing date of Jan. 30$^{th}$, 2004, designating the United States of America, and claims the benefit of British Patent Application No. 0302378.5, which was filed Feb. 1, 2003.

BACKGROUND AND SUMMARY OF THE INVENTION

The present invention relates to a detection system, and particularly though not exclusively to a detection system suitable for detecting circular dichroism.

Circular dichroism is the differential absorption between left and right circularly polarised light on passage through a sample. When light passes through a sample, linear absorbance of the light occurs with the result that the amount of light that passes from the sample is less than the amount of light that passed into the sample. Measuring this difference provides a measurement of the linear absorbance of the sample. When the light is circularly polarised a secondary absorbance component arises from circular dichroism. The secondary absorbance component is measured by switching between left and right circularly polarised light, and measuring the resulting difference in absorbance.

Measurement of circular dichroism gives detailed structural and enantiomeric (handedness) information on proteins, carbohydrates, nucleic acids, pharmaceuticals, liquid crystals, etc. With circular dichroism one can follow e.g. the conversion of simple peptides into the destructive fibrils of CJD, Alzheimer's, cystic fibrosis etc. Handedness was at the heart of the thalidomide disaster.

Since circular dichroism is a secondary component of the measurement of absorbance, it is a difficult property to measure. Typically the absorbance due to circular dichroism is around one part in $10^5$ of the mean intensity of light transmitted by a sample. Measurement is further complicated by the fact that absorbance measurements are often performed at ultraviolet and deep ultraviolet wavelengths (i.e. <200 nm).

It is conventional to detect circular dichroism by modulating the polarisation of light incident on a sample using a polarising modulator, and then detecting the modulation of light transmitted by the sample using phase-locked detection. The polarising modulator is for example configured to switch the polarisation of the incident light beam between left hand polarisation and right hand polarisation at a frequency of 50 kHz, and the phase-locked detector measures at 50 kHz light incident upon the detector. This allows detection of circular dichroism which effectively comprises a small AC signal on a very large DC background.

Conventionally, a single element detection system is used to detect circular dichroism. The system comprises a photo multiplier tube with a high dynamic range (typically $10^9$), coupled to a phase-locked signal extraction amplifier that is able to distinguish the circular dichroism signal from the background signal. The detection system uses a servo system to adjust the high tension on the photo multiplier to produce a constant DC current output, independent of the intensity of DC light incident upon the photo multiplier tube. This is done to compensate for changes of beam intensity and of linear absorbance as the wavelength of the incident light is scanned (the beam intensity and linear absorbance may change by four orders of magnitude). The constant DC current output is advantageous because it provides a constant DC level from which the AC circular dichroism signal may be easily phase-lock extracted.

The wavelength range of interest is scanned wavelength by wavelength (with about 1 nm resolution). The scanning process takes many minutes when the circular dichroism signal is strong, but many hours when the circular dichroism signal is weaker (as is the case for most useful circular dichroism work).

It is an object of the present invention to provide a detection system which overcomes or mitigates at least one of the above disadvantages.

According to a first aspect of the invention there is provided a detection system comprising modulation means for applying a modulation to an incident beam of radiation, sample holding means through which the modulated beam of radiation is passed, beam expansion means to expand the beam of radiation, an array of solid state detectors arranged to receive different parts of the expanded beam of radiation, and processing means arranged to synchronise detected signals with the modulation applied by the modulation means.

The detection system is advantageous because the use of an array of solid state detectors, rather than the single detector used by the prior art, allows more information to be determined from the detected signals.

Preferably, the processing means further comprises amplification means to amplify signals detected by the array of solid state detectors.

The detectors are preferably solid state detectors although other forms of detector, such as for instance multi-channel photo-multipliers could be used.

Preferably, the processing means further comprises digitisation means to digitise detected signals.

Preferably, the processing means is arranged to digitise detected signals before they are synchronised with the modulation applied by the modulation means. This is advantageous as compared to the conventional approach of synchronising before digitisation, since it provides faster and more sensitive measurement.

The beam expansion means may comprise wavelength separation means arranged to convert the beam of radiation into a diverging fan of wavelengths.

Preferably, the wavelength separation means comprises a reflective grating.

Preferably, the system further comprises a steering mirror, the orientation of the steering mirror being adjustable to allow selection of the wavelengths of the fan that are incident upon the array of solid state detectors.

The beam expansion means may comprise means for expanding the beam of radiation whilst retaining spatial properties of the beam in at least one direction perpendicular to the direction of propagation of the beam of radiation.

Preferably, the array of solid state detectors is a two dimensional array.

Wavelength separation may be provided in a first direction perpendicular to the direction of propagation of the beam of radiation, and beam expansion whilst retaining spatial properties may be provided in a second direction perpendicular to the direction of propagation of the beam of radiation, the two dimensional array being used to detect wavelength dependent properties and spatial properties of the expanded beam.

Preferably, the array of solid state detectors comprises a first array of photodiodes arranged to detect near ultraviolet wavelengths, and a second array of photodiodes arranged to detect deep ultraviolet wavelengths.

Preferably, the first array of photodiodes comprises silicon.

Preferably, the second array of photodiodes comprises AlGaN.

Preferably, the modulation means is configured to apply a modulated circular polarisation to the beam of radiation. It will be appreciated that other forms of modulation may be applied to the beam of radiation.

Preferably, the modulation means is configured to apply a modulation at a frequency greater than 1 kHz.

Preferably, the sample holding means is provided with an adjustable aperture, which allows adjustment of the width of beam incident upon a sample.

Preferably, each detector of the array of solid state detectors is provided with a transconductance amplifier arranged to convert photocurrent output by the detector into a voltage.

Preferably, the transconductance amplifier is provided with a plurality of resistors which may be connected to the transconductance amplifier in different combinations using a switch, to modify the gain of the transconductance amplifier.

Preferably, the switch is controlled by a microprocessor.

Preferably, each detector of the array of solid state detectors is provided with an AC amplifier arranged to amplify AC components of a signal detected by the solid state detector.

Preferably, the AC amplifier is provided with a plurality of resistors which may be connected to the transconductance amplifier in different combinations using a switch, to modify the gain of the AC amplifier.

Preferably, the switch is controlled by a microprocessor.

Preferably, the system is provided with a band pass filter tuned to the frequency of operation of the modulation means.

Preferably, the system further comprises a multiplexor arranged to multiplex, for each detector of the array of solid state detectors, a DC signal and an AC signal after amplification.

Preferably, synchronisation is performed by a field programmable array. The skilled person will appreciate that a field programmable array (FPGA) is a known form of commercially available programmable electronic circuit which may be integrated on a single chip with very fast operation and small size. A single chip may contain very large numbers (in excess of 20,000) semi conductor gates that can be configured to form descrete electronic function circuits, such as adders and the like. The circuit can then be programmed to perform arithmetic operations, such as addition, subtraction and division, very rapidly. The ability to re-configure such arrays is an advantage over existing ASIC technology.

Preferably, the system further comprises a personal computer arranged to receive data, and to control operation of components of the system.

Preferably, the array of solid state detectors is translatable and pivotable to allow it to be aligned with the beam.

According to a second aspect of the invention there is provided a detection system comprising modulation means for applying a modulation to an incident beam of radiation, sample holding means through which the modulated beam is passed, at least one solid state detector, and processing means arranged to amplify and digitise signals detected by the at least one detector, and then to subsequently synchronise the amplified and digitised signal with the modulation applied by the modulation means.

The second aspect of the invention is advantageous because it provides detection which is faster and more sensitive than conventional circular dichroism measurement systems, where the signal is synchronised with the polarising modulator before it is digitised.

The second aspect of the invention may further comprise any of the preferred features of the first aspect of the invention.

According to a third aspect of the invention there is provided a detection method comprising applying a modulation to an incident beam of radiation, passing the modulated beam of radiation through a sample held in a sample holding means, expanding the beam of radiation, detecting different part of the expanded beam of radiation using an array of solid state detectors, synchronising detected signals with the applied modulation.

Preferably, the detected signals are amplified.

Preferably, the detected signals are digitised.

Preferably, the detected signals are digitised before they are synchronised with the applied modulation.

According to a fourth aspect of the invention there is provided a detection method comprising applying a modulation to an incident beam of radiation, passing the modulated beam of radiation through a sample, detecting the beam of radiation using at least one solid state detector, amplifying and digitising the signals detected by the at least one detector, and then subsequently synchronising the amplified and digitised signals with the applied modulation.

The fourth aspect of the invention may further comprise any of the preferred features of the second aspect of the invention.

BRIEF DESCRIPTION OF THE DRAWINGS

A specific embodiment of the invention will now be described by way of example only, with reference to the accompanying figures, in which.

DETAILED DESCRIPTION OF THE INVENTION

Figure 1:
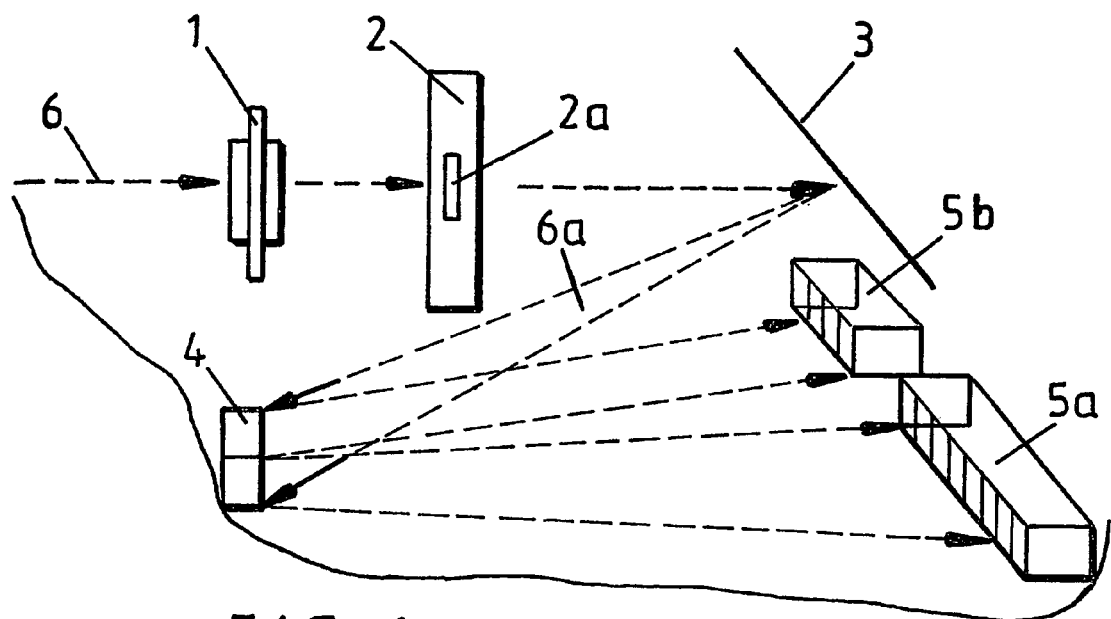
FIG. 1 is a schematic perspective view of optical components of an embodiment of the invention.

Referring to FIG. 1, optical components of a detection system comprise a polarising modulator 1, a sample cell 2, a reflective grating 3, a mirror 4, and detector arrays 5a, 5b. A beam 6 of synchrotron radiation, which comprises electromagnetic radiation at an ultraviolet wavelength, is directed through the polarising modulator 1. The polarising modulator 1, which is electrostatic, is switched at a frequency of 50 kHz and polarises the ultraviolet beam of radiation to have a left or right handed circular polarisation (the handedness of the polarisation switches at 50 kHz).

The polarised beam 6 passes through the sample cell 2, which contains a protein sample. The sample cell 2 is provided with an aperture 2a which is adjustable in size, the aperture 2a typically being arranged to allow a beam of approximately 4 mm diameter into the sample cell 2. The polarised beam 6 is absorbed by the protein sample, linear absorption occurring together with absorption due to circular dichroism. Upon exiting the sample cell, the attenuated beam 6 comprises a DC component and a low intensity 50 kHz AC component (the AC component arising from the dichroic absorption of the polarisation modulated light).

The beam 6 passes to the reflective grating 3, which has a 1 nm per mm dispersion characteristic. The grating separates the beam 6 into a fan 6a of different wavelengths, as shown schematically in FIG. 1. The fan 6a is incident upon the mirror 4 which, in addition to steering the fan 6a to the detector arrays 5a, 5b is used to provide wavelength band selection. The detector arrays 5a, 5b comprise a first silicon array 5a which is capable of detecting near ultraviolet, and a second AlGaN array 5b which is capable of detecting deep ultraviolet.

Figure 2:
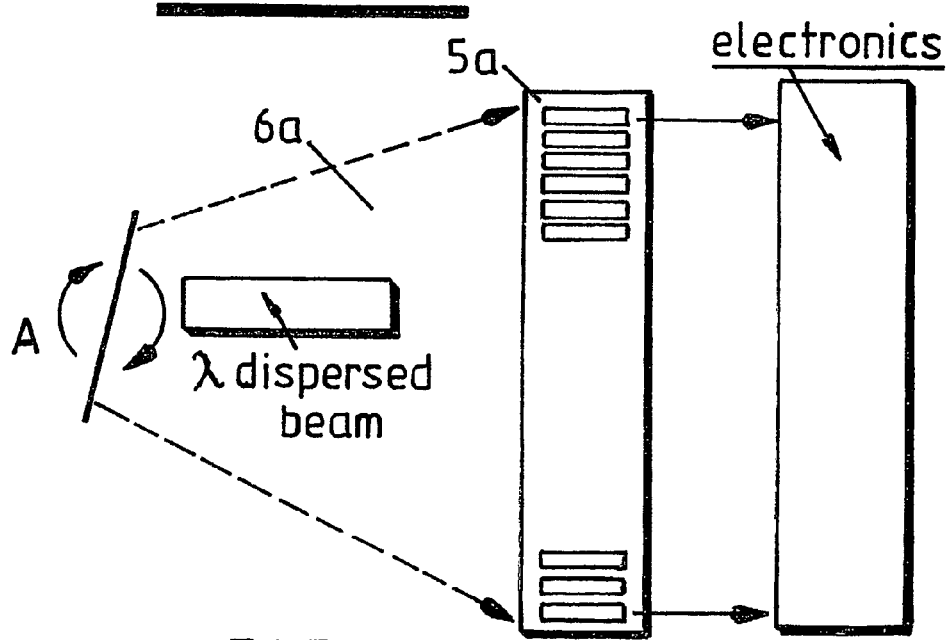
FIG. 2 is a schematic view from above of part of FIG. 1.

FIG. 2 shows the steering mirror 4 and the near UV detector array 5a from above. The detector array 5a comprises a linear array of silicon photodiodes, which are manufactured by Hamamatsu Photonics KK of Japan (product number 4114-46Q-SP). The array comprises 46 photodiodes each 4.6 by 0.9 mm. It will be appreciated that, since the fan 6a provides wavelength separation, each photodiode will detect a different wavelength of light. The wavelength detected by each photodiode may be adjusted by rotating the steering mirror 4. Rotation of the steering mirror 4 in the clockwise direction, as shown by the arrows A in FIG. 2, will move shorter wavelengths onto the detector array 5a, and move longer wavelengths off the detector array 5a. Rotation of the steering mirror 4 in the anticlockwise direction will move longer wavelengths onto the detector array 5a, and move shorter wavelengths off the detector array 5a. The wavelength band detected by each photodiode may be broadened or narrowed by increasing or decreasing respectively the path length between the reflective grating 3 and the array 5a. Alternatively, a reflective grating 3 with a different dispersion characteristic may be used. Output signals from the array 5a are passed to electronics which are described in detail further below.

The optical components of the detection system, as shown in FIGS. 1 and 2, are advantageous because they allow simultaneous parallel detection of light at different wavelengths, instead of requiring serial wavelength measurements as is the case with the prior art. This allows circular dichroism (circular dichroism) measurements to be made quickly, in the order of seconds or faster, rather than over several hours.

Figure 3:
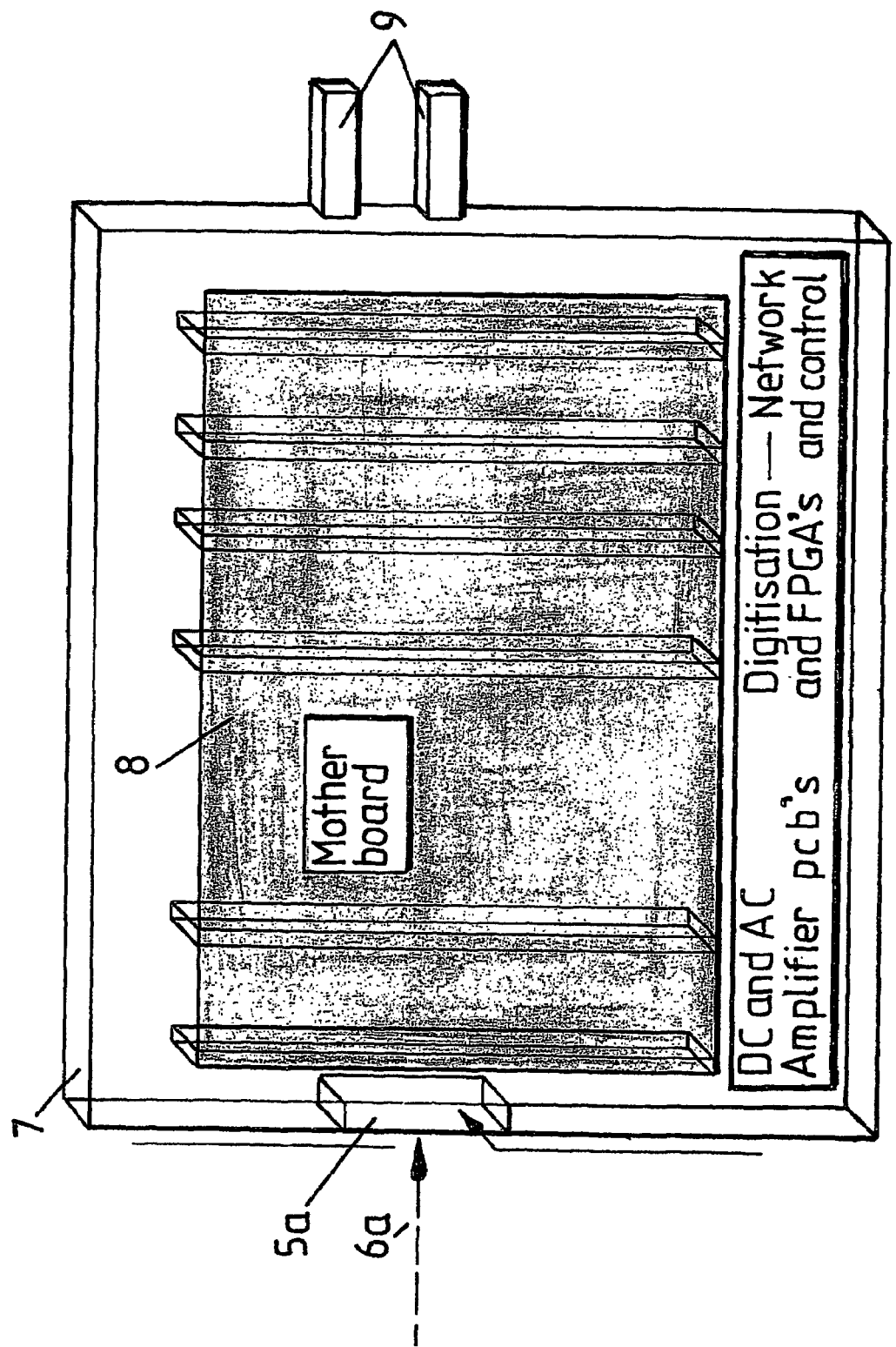
FIG. 3 is a schematic view of the physical configuration of electronic component of the embodiment of the invention.

Referring to FIG. 3, the detector array 5a is located at a left hand end of a box 7. The box contains a mother board 8 onto which electronics used to process signals output by the sensor array 5a are located. Buses 9 carry data from the electronics to a personal computer (PC). The box 7 is mounted upon a translatable mounting which allows the box 7 to be translated accurately in any required direction. The mounting also includes pivot controls which allow the box 7 to be angled in any direction. This combination of translation and pivoting is advantageous because it allows the sensor array 5a to be located in a preferred region of the dispersed ultraviolet beam and at a preferred angle.

Figure 4:
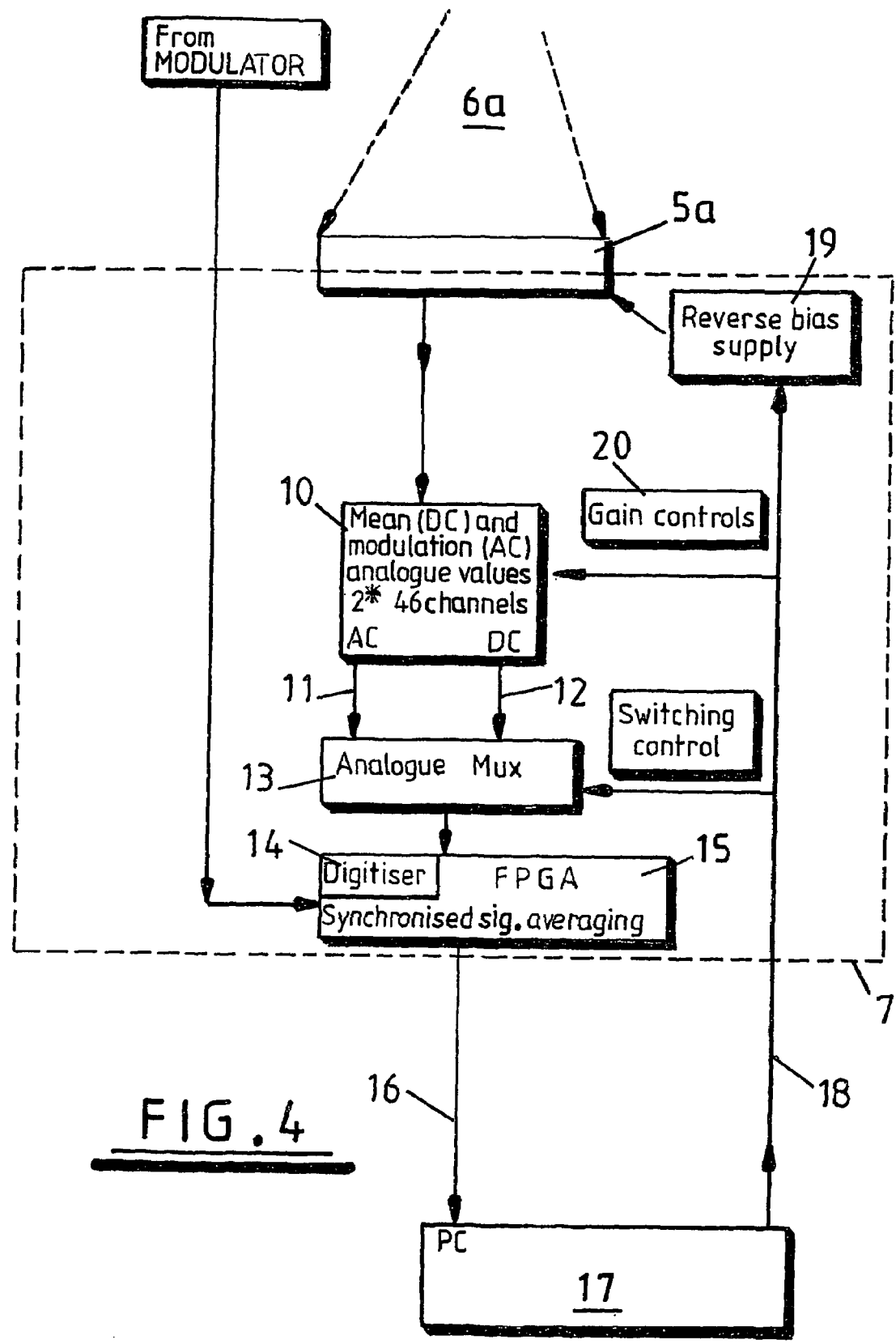
FIG. 4 is a schematic diagram showing the electronic components of the embodiment of the invention.

FIG. 4 shows schematically the electronics held within the box 7. The sensor array 5a is located at an exterior wall of the box 7 as shown. Photocurrents output from each photodiode of the sensor array 5a are passed to AC and DC gain controlled amplifiers 10. The photocurrents are shown as passing via a single connection 10a for ease of illustration (a separate connection is provided for each photodiode of the sensor array 5a).

The DC gain controlled amplifier is a transconductance amplifier, and is used to convert the photodiode photocurrent into an output voltage. The AC gain controlled amplifier amplifies the AC component of the photocurrent, and provides an AC voltage output 11. The DC gain controlled amplifier amplifies the DC component of the photocurrent, and provides a DC voltage output 12. Separate amplifiers 10 and outputs 11, 12 are provided for each photodiode of the sensor array 5a, although only one is shown in FIG. 4 for ease of illustration.

A multiplexor 13 is used to multiplex the AC and DC signals such that an AC signal relating to a given photodiode channel is multiplexed with a DC signal for that channel. In FIG. 4 only one output signal is shown for ease of illustration, whereas the multiplexor 13 has 46 outputs. The use of the multiplexor is advantageous because it reduces the number of data carrying channels from 92 (separate AC and DC channels for each photodiode) to 46 (a single channel carrying multiplexed AC and DC for each photodiode). The multiplexor outputs the multiplexed photodiode signals to a digitiser 14. The digitiser 14 digitises analogue voltages to 12 bits, 4096 levels, at 33 MHz.

Following digitisation, the AC signals are synchronised to the modulation of the polarising modulator (1 in FIG. 1) by a field programmable array 15. The fast programmable array (FPGA) comprises three 16 channel FPGA's. These are programmed in firmware to perform the synchronisation. All output signals are treated in parallel by the FPGA, thereby synchronising all of the signals with respect to the modulation of the polarising modulator. The FPGA's are programmed to, integrate the signal average over a selected number of synchronisation periods. The synchronisation period depends on the frequency of modulation of the polarising modulator, and will typically be of the order of 20 micro seconds for a full period (comprising two half periods of 10 micro seconds which determine the left and right handed intervals of polarisation). In application other than CD detection, faster modulation could be used with synchronisation periods down to the digitialisation time (typically 50 nano seconds) or better. Each period of left and right-handed polarisation is detected and integrated separately. Integration is performed to average the required signal by adding the digital values of the selected sample within each synchronisation period and then add together a selected number of synchronisation periods for each polarisation and divide by the total number of samples.

The digital signal output by the FPGA's is passed via a 32 bit digital bus 16 to a PC 17 for processing. The PC 17 determines the integration period for signal measurement, subtracts background signals from measured signals, determines the ratio of modulated signal to mean signal (AC to DC) levels, stores data, and displays instantaneous and integrated data. In addition, the PC 17 controls via a control output 18 operation of components located within the box 7. The PC 17 controls the reverse bias which is supplied to the sensor array 5a by a reverse bias supply 19, thereby controlling the sensitivity of the sensor array 5a. The PC 17 also controls the gain of the AC and DC amplifiers via gain controls 20. In addition, the PC 17 controls operation of the analogue multiplexor 13.

Figure 5:
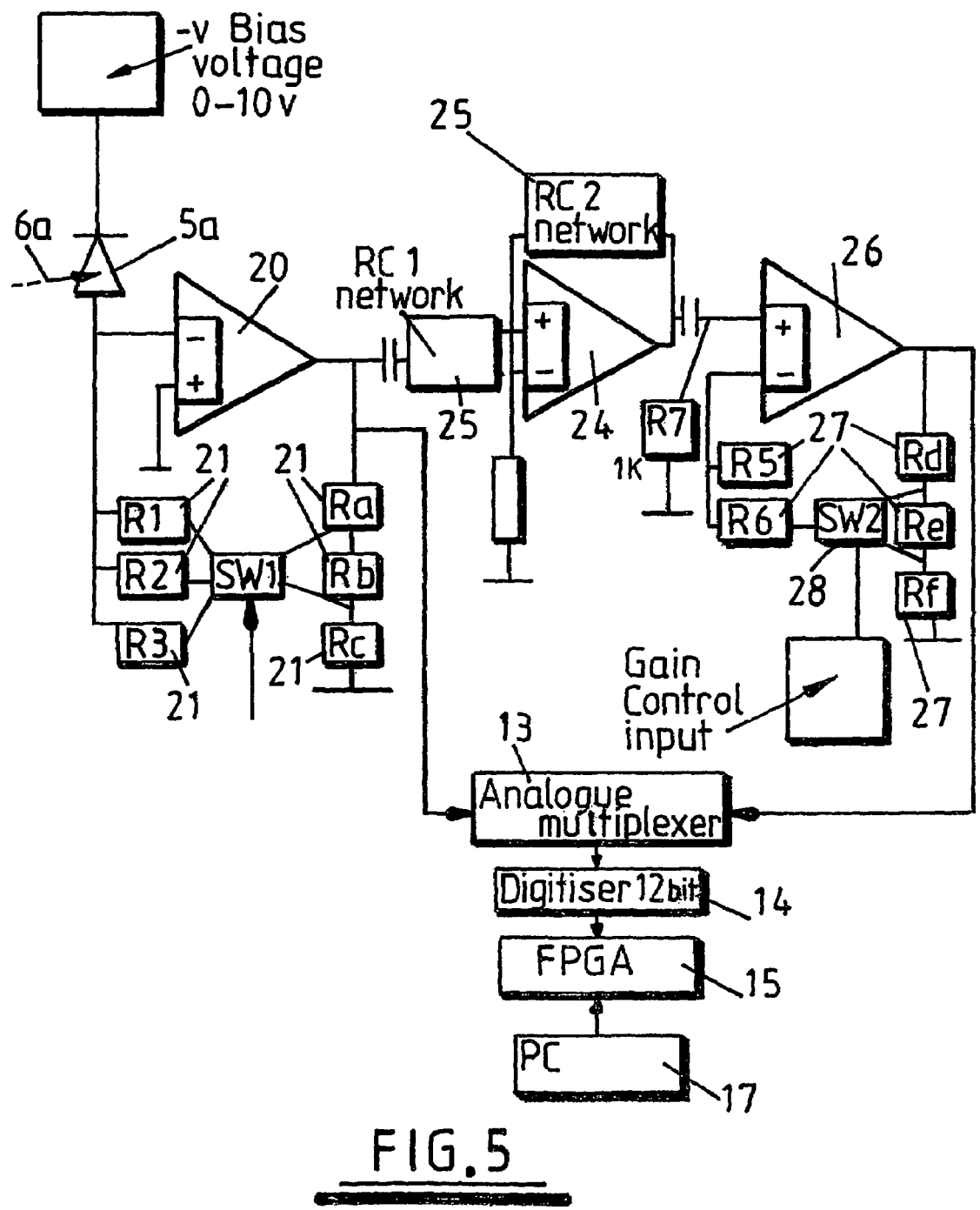
FIG. 5 is a schematic circuit diagram showing part of the circuit in more detail.

The AC and DC amplifier 10 will now be described in more detail, with reference to FIG. 5. A single photodiode 5c of the photodiode array 5a is shown in FIG. 5. Similarly, a single AC and DC amplifier arrangement is shown rather than the 46 amplifier arrangements that are used to amplify signals generated by each photodiode 5c of the photodiode array 5a. The photocurrent output from the photodiode 5c passes to an inverting input of a transimpedance amplifier 20. The transimpedance amplifier 20 amplifies the DC component and the AC component of the signal (i.e. the entire signal is amplified), and provides an output voltage. The gain provided by the transimpedance amplifier 20 is determined by feedback resistors 21. The gain is adjusted by selecting combinations of resistors 21 using a switch 22 which is controlled by the PC 17 (see FIG. 4). An output from the transimpedance amplifier 20 is split to provide two signals. The capacitor 23 allows the majority of the AC component of the signal output by the transimpedance amplifier 20 to pass to a band pass amplifier 24, whereas a substantially DC signal is passed to the multiplexor 13.

Gain control steps of factors of 10 in the DC stage are required to compensate for the variation of DC beam absorption with respect to wavelength. The DC beam absorption will vary by a factor of 100 between 190 nm and 200 nm. In prior art photo-multiplier tubes the gain must be continually adjusted as the wavelength of the light changes. In contrast to this, when the invention is used the wavelength of light detected by each photodiode does not change over time. This means that the gain may be set separately for each photodiode (each photodiode detects a different wavelength) and may then remain fixed. This is a substantial advantage over the prior art. In addition, the fact that detection for all wavelengths takes place during a time period of a few seconds means that gain does not need to be adjusted to take account of time dependent variation of beam intensity (the time scale for such variations is around 1 hour).

The combination of resistors which is used provide gain adjustment is set out on the following table:

| R1 | 200K | Ra | 50K * 1 |
|---|---|---|---|
| R2 | 2 M | Rb | 25K * 2 |
| R3 | 10 M | Rc | 25K * 4 |

Different combinations of these resistors are connected together using the switch 22.

The capacitor 23 allows the AC components of the signal output by the transimpedance amplifier 20 to pass to a 50 kHz band pass amplifier 24. A RC network 25 is used to tune the amplifier 24 to 50 kHz. A separate amplifier 26 provides controlled gain for the 50 kHz signal, the gain being selected by selecting a combination of resistors 27 using a switch 28. The gain is controlled by the PC 17 (see FIG. 4). The output signal is passed to the analogue multiplexor 13. Subsequent components of the system are as described in relation to FIG. 4.

The magnitude of the AC circular dichroism signal will vary, for example due to protein to protein variation. The variation is likely to be by roughly factors of 2. These are compensated for using the resistors 27, values of which are given in the following table:

|  |  | Rd | 17K * 1.0 |
|---|---|---|---|
| R5 | 200K * 200 | Re | 16K * 1.2 |
| R6 | 400K * 400 | Rf | 66k * 1.5 |

The switches 22, 28 are controlled by the PC 17, which specifies the switch settings for each photodiode 5c. The switch 22 at the DC amplifier may provide nine different gain options, and these may be specified using a 4-bit code. The switch 28 at the AC amplifier may provide six different gain options, and these may be specified using a 3-bit code. Hence, the PC 17 is able to specify a given photodiode 5c, and specify DC and AC gain for that photodiode using a 16-bit word (the switches 22, 28 are controlled digitally). The configuration of the switches may be changed between measurements to provide desired DC and AC gains.

Two amplifiers 20, 26 are used to provide independently adjustable gain for the DC signal and the AC signal, in order to obtain a circular dichroic signal with an optimum signal to noise ratio. The peak photodiode current is around 4.8 μA per photodiode of the array 5a. This means that the transimpedance amplifier 20 has a transimpedance of 200 kΩ, to obtain an output of 1V. The AC gain control amplifier 26 provides a voltage gain of 500, to provide an AC signal output with a peak-to-peak value of approximately 1V (this is based upon the AC signal being 1/500 of the DC signal).

Communication between the PC 17 and the FPGA 15 and other components of the detection system electronics is provided by an Ethernet link. The Ethernet link carries control signals to the detection system electronics, for example the gain control signal described above. Other control signals carried by the Ethernet link include signal averaging and integration commands, and control signals for the multiplexor 13. The integration period may vary between 10 microseconds (1 sync pulse period) and 10 seconds.

The Ethernet link carries raw spectrum data from the detection system electronics after collection (the spectrum data comprises both DC and AC data). The data is stored in the FPGA's during collection.

A display unit (not shown) is connected to the PC, and is used to display DC and $AC_{p-p}$ (peak to peak) spectra. The display also shows the circular dichroism spectra as calculated by the PC (circular dichroism=$AC_{p-p}$/DC).

Photodiodes are available which may be used as an alternative to the silicon photodiodes described above. For instance, photodiodes manufactured by United Detector Technology may be used to detect deep ultraviolet signals (i.e. <200 nm) or calibrated to operate in the near ultraviolet wavelength region.

Although FIGS. 2, 3 and 4 have been described with reference to the near UV detector array 5a, it will be appreciated that the deep UV detector array 5b of $Al_xGa_{1-x}N$ photodiodes may be connected, used, and the signals generated from those photodiodes processed, in an essentially identical fashion.

The use of $Al_xGa_{1-x}N$ to detect deep UV is well known. A typical deep UV detector array 5b may comprise a ternary $Al_xGa_{1-x}N$ (Aluminium Gallium Nitride) compound semiconductor as its active, or UV detecting material. $Al_xGa_{1-x}N$ is a direct bandgap semiconductor, therefore having greater absorption efficiency than indirect bandgap semiconductors. In this particular compound, a subscript 'x' denotes the percentage (or 'atomic ratio') of Al in a specific compound and hence the ratio of Al:Ga in the ternary compound semiconductor. For example, for a 40% Al content, the ternary compound $Al_xGa_{1-x}N$ would read $Al_{40}Ga_{60}N$.

UV detectors made from $Al_xGa_{1-x}N$ have a tuneable cutoff wavelength between 365 nm and 200 nm, a specific wavelength being defined by selecting and implementing an appropriate value for the atomic ratio 'x'. Above this cutoff wavelength, little or no radiation is detected. Thus the deep UV detector array 5b can be tuned to have an upper cutoff wavelength that slightly overlaps the detectable range of the near UV detector 5a, whilst having a greater detection efficiency in the deep UV thus complimenting the near UV detector array 5b. By having a near UV detector array 5a and a deep UV detector array, each array 5a, 5b can be optimised for, or tuned to, a particular part of a (UV) spectrum. The upper cutoff wavelength may also be defined by an experimental region of interest. For example, in CD measurement, the upper cutoff may conveniently be 260 nm. To achieve this value, the atomic ratio 'x' is substantially 40%. The atomic ratio may be greater than 40%, thus increasing the range of detectable wavelengths by increasing the value of the upper cutoff wavelength.

Undoped AlGaN layers may be grown on a sapphire substrate using epitaxial methods, such as Metal Organic Chemical Vapour Deposition (MOCVD) or Molecular Beam Epitaxy (MBE). The AlGaN layer and sapphire substrate each have a lattice constant. If the lattice constants are not substantially equivalent (mismatched), crystal defects, such as cracks, may form in the AlGaN layers. To prevent this from occurring, the mismatch in lattice constants must be reduced. Thus any strain on the AlGaN layers due to the mismatch is reduced, and the probability of any resultant defects occurring reduced accordingly. This is achieved by growing a layer between the AlGaN layer and the sapphire substrate with a lattice constant of a value that is between that of the AlGaN layer and sapphire substrate. Such a layer may be a GaN layer. Furthermore, to optimise growth of the layers and to prevent the propagation of any cracks that may, nevertheless, develop, the AlGaN layers may be graded or be interspersed with thin AlN (Aluminium Nitride) layers.

Interdigitated photo-detecting structures are formed on the $Al_xGa_{1-x}N$ material using metal-semiconductor-metal configurations with alternate Schottky-Ohmic contacts. The size of the photo-detecting structures and any gaps between them may be varied according to the application. For example, the structures and their dimensions may be optimised with respect to response time and/or signal strength.

It will be appreciated that in timing the cutoff wavelength of the $Al_xGa_{1-x}N$, the range of wavelengths which the deep UV detector array 5b can detect is also tuneable. Thus, if detection of wavelengths above a certain value is undesirable, the upper limit of this range can be defined to exclude these wavelengths. It will be appreciated that by excluding undesirable wavelengths, this may improve the signal to noise ratio of any measurements made by reducing background noise.

The active, or UV detecting material may be another material with a high absorption efficiency with regard to deep UV radiation. Such a material may be SiC (Silicon Carbide) or Diamond. It will also be appreciated that a substrate of a material other than sapphire may be used. The substrate must have a good crystal quality, chemical inertness and thermal matching. In the case of light detectors, the layer must be transparent. For example, Si (111) may be used as the substrate material.

Although the composition of the deep UV detector array 5b may vary, it will be appreciated that regardless of this fact, the detection system itself operates in an identical manner.

The detection system described above may be operated for capture times of 50 ns or lower. This means that fast changes of circular dichroism with respect to time may be measured using the detection system, the measurements being wavelength resolved.

The invention may be used to provide spatial image measurements of circular dichroism. This is done by replacing the reflective grating 3 with reflective optics which expand the beam 1 such that different spatial zones of the beam are incident upon different photodiodes 5c of the array 5a (or 5b). The photodiode array 5a (or 5b) may be replaced with a two-dimensional array to allow two-dimensional spatial imaging.

A mixture of wavelength resolved and spatial imaging measurements may be obtained using the invention. This may be done for example by using a combination of the reflective grating 3 to obtain wavelength resolution in the horizontal direction, and beam expansion optics arranged to spatially expand the beam in the vertical direction (a two-dimensional array is required when this is done).

The detection system works in a manner which is completely opposite to the conventional measurement of circular dichroism. The detection system amplifies and digitises detected signals, and then subsequently synchronises the signals with the polarising modulator. This is faster and more sensitive than conventional circular dichroism measurement systems, where the signal is synchronised with the polarising modulator before it is digitised.

The amplification and detection, together with the digitisation and synchronisation is performed by the detection using firmware. This allows the detection system to operate at high speeds (50 ns capture times or lower), allowing time resolved measurements to be performed.

Although the described embodiment of the invention relates to the measurement of circular dichroism, it will be appreciated that the invention may be used for other applications requiring the extraction of a small modulated signal from a high background signal. Examples include laser pulsed florescence and synchronisation to a synchrotron radiation.

The invention claimed is:

1. A circular dichroism detection system comprising a modulator to apply a modulation to an incident beam of radiation, a sample cell through which the modulated beam of radiation is passed, a beam expander to expand the beam of radiation, an array of detectors arranged to receive different parts of the expanded beam of radiation, and a processor arranged to synchronise detected signals with the modulation applied by the modulator, wherein the modulator is configured to apply a modulated circular polarisation to the beam and is configured to apply a modulation at a frequency greater than 1 kHz, the processor further comprising a digitiser arranged to digitise detected signals before they are synchronised with the modulation applied by the modulator.

2. The circular dichroism detection system according to claim 1, wherein the detectors are solid state detectors.

3. The circular dichroism detection system according to claim 2, wherein the processing means further comprises an amplifier to amplify signals detected by the array of solid state detectors.

4. The circular dichroism detection system according to claim 1, wherein the beam expander comprises a wavelength separator arranged to convert the beam into a diverging fan of wavelengths.

5. The circular dichroism A detection system according to claim 4, wherein the wavelength separator comprises a reflective grating.

6. The circular dichroism detection system according to claim 4, wherein the system further comprises a steering mirror, the orientation of the steering mirror being adjustable to allow selection of the wavelengths of the fan that are incident upon the array of detectors.

7. The circular dichroism detection system according to claim 1, wherein the beam expander comprises optics to expand the beam of radiation whilst retaining spatial properties of the beam of radiation in at least one direction perpendicular to the direction of propagation of the beam of radiation.

8. The circular dichroism detection system according to claim 2, wherein the array of solid state detectors is a two dimensional array.

9. The circular dichroism detection system according to claim 4, wherein wavelength separation is provided in a first direction perpendicular to the direction of propagation of the beam of radiation, and beam expansion whilst retaining spatial properties is provided in a second direction perpendicular to the direction of propagation of the beam of radiation, the two dimensional array being used to detect wavelength dependent properties and spatial properties of the expanded beam.

10. The circular dichroism detection system according to claim 2, wherein the array of solid state detectors comprises a first array of photodiodes arranged to detect near ultraviolet wavelengths, and a second array of photodiodes arranged to detect deep ultraviolet wavelengths.

11. The circular dichroism detection system according to claim 10, wherein the first array of photodiodes is a silicon photodiode array.

12. The circular dichroism detection system according to claim 10, wherein the second array of photodiodes is an AlGaN photodiode array.

13. The circular dichroism detection system according to claim 1, wherein the sample cell is provided with an adjustable aperture, which allows adjustment of the width of beam incident upon a sample.

14. The circular dichroism detection system according to claim 2, wherein each detector of the array of solid state detectors is provided with a transconductance amplifier arranged to convert photocurrent output by the detector into a voltage.

15. The circular dichroism detection system according to claim 14, wherein the transconductance amplifier is provided with a plurality of resistors which may be connected to the transconductance amplifier in different combinations using a switch, to modify the gain of the transconductance amplifier.

16. The circular dichroism detection system according to claim 15, wherein the switch is controlled by a microprocessor.

17. The circular dichroism detection system according to claim 2, wherein each detector of the array of solid state detectors is provided with an AC amplifier arranged to amplify AC components of a signal detected by the solid state detector.

18. The circular dichroism detection system according to claim 17, wherein the AC amplifier is provided with a plurality of resistors which may be connected to the transconductance amplifier in different combinations using a switch, to modify the gain of the AC amplifier.

19. The circular dichroism detection system according to claim 18, wherein the switch is controlled by a microprocessor.

20. The circular dichroism detection system according to claim 1, wherein the system is provided with a band pass filter tuned to the frequency of operation of the modulator.

21. The circular dichroism detection system according to claim 2, wherein the system further comprises a multiplexor arranged to multiplex, for each detector of the array of solid state detectors, a DC signal and an AC signal after amplification.

22. The circular dichroism detection system according to claim 1, wherein synchronisation is performed by a fast programmable array.

23. The circular dichroism detection system according to claim 1, wherein the system further comprises a personal computer arranged to receive data, and to control operation of components of the system.

24. The circular dichroism detection system according to claim 2, wherein the array of solid state detectors is translatable and pivotable to allow it to be aligned with the beam.

25. A circular dichroism detection system comprising a modulator to apply a modulation to an incident beam of radiation, a sample cell through which the modulated beam is passed, at least one solid state detector, and processor arranged to amplify and digitise signals detected by the at least one detector, and then to subsequently synchronise the amplified and digitised signal with the modulation applied by the modulator, wherein the modulator is configured to apply a modulated circular polarisation to the beam and is configured to apply a modulation at a frequency greater than 1 kHz, the processor further comprising a digitiser arranged to digitise detected signals before they are synchronized with the modulation applied by the modulator.

26. A circular dichroism detection method comprising applying a modulation to an incident beam of radiation, passing the modulated beam of radiation through a sample held in a sample cell, expanding the beam of radiation, detecting different part of the expanded beam of radiation using an array of solid state detectors, synchronising detected signals with the applied modulation, wherein applying the modulation includes applying a modulated circular polarization to the beam and applying the modulation at a frequency of greater than 1 kHz and digitising the detected signals before they are synchronized with the applied modulation.

27. The circular dichroism detection method according to claim 26, wherein the detected signals are amplified.

28. A circular dichroism detection method comprising applying a modulation to an incident beam of radiation, passing the modulated beam of radiation through a sample, detecting the beam of radiation using at least one solid state detector, amplifying and digitising the signals detected by the at least one detector, and then subsequently synchronising the amplified and digitised signals with the applied modulation, wherein applying the modulation includes applying a modulated circular polarization to the beam and applying the modulation at a frequency of greater than 1 kHz and digitising the detected signals before they are synchronized with the applied modulation.

29. The circular dichroism detection system according to claim 3, wherein the processor further comprises a digitiser to digitise detected signals.

30. The circular dichroism detection system according to claim 29, wherein the processor is arranged to digitise detected signals before they are synchronised with the modulation applied by the modulator.

31. The circular dichroism detection system according to claim 1, wherein the beam expander comprises a wavelength separator arranged to convert the beam into a diverging fan of wavelengths.

32. The circular dichroism detection system according to claim 2, wherein the beam expander comprises a wavelength separator arranged to convert the beam into a diverging fan of wavelengths.

33. The circular dichroism detection system according to claim 32, wherein the wavelength separator comprises a reflective grating.

34. The circular dichroism detection system according to claim 5, wherein the system further comprises a steering mirror, the orientation of the steering mirror being adjustable to allow selection of the wavelengths of the fan that are incident upon the array of detectors.

35. The circular dichroism detection system according to claim 2, wherein the system further comprises a steering mirror, the orientation of the steering mirror being adjustable to allow selection of the wavelengths of the fan that are incident upon the array of solid state detectors.

36. The circular dichroism detection system according to claim 34, wherein the beam expander comprises optics to expand the beam of radiation whilst retaining spatial properties of the beam of radiation in at least one direction perpendicular to the direction of propagation of the beam of radiation.

37. The circular dichroism detection system according to claim 35, wherein the array of solid state detectors is a two dimensional array.

38. The circular dichroism detection system according to claim 7, wherein wavelength separation is provided in a first direction perpendicular to the direction of propagation of the beam of radiation, and beam expansion whilst retaining spatial properties is provided in a second direction perpendicular to the direction of propagation of the beam of radiation, the two dimensional array being used to detect wavelength dependent properties and spatial properties of the expanded beam.

39. The circular dichroism detection system according to claim 8, wherein wavelength separation is provided in a first direction perpendicular to the direction of propagation of the beam of radiation, and beam expansion whilst retaining spatial properties is provided in a second direction perpendicular to the direction of propagation of the beam of radiation, the two dimensional array being used to detect wavelength dependent properties and spatial properties of the expanded beam.

40. The circular dichroism detection system according to claim 36, wherein wavelength separation is provided in a first direction perpendicular to the direction of propagation of the beam of radiation, and beam expansion whilst retaining spatial properties is provided in a second direction perpendicular to the direction of propagation of the beam of radiation, the two dimensional array being used to detect wavelength dependent properties and spatial properties of the expanded beam.

41. The circular dichroism detection system according to claim 39, wherein the array of solid state detectors comprises a first array of photodiodes arranged to detect near ultraviolet wavelengths, and a second array of photodiodes arranged to detect deep ultraviolet wavelengths.

42. The circular dichroism detection system according to claim 11, wherein the second array of photodiodes is an AlGaN photodiode array.

43. The circular dichroism detection system according to claim 41, wherein the sample cell is provided with an adjustable aperture, which allows adjustment of the width of beam incident upon a sample.

44. The circular dichroism detection system according to claim 42, wherein each detector of the array of solid state detectors is provided with a transconductance amplifier arranged to convert photocurrent output by the detector into a voltage.

45. The circular dichroism detection system according to claim 16, wherein each detector of the array of solid state detectors is provided with an AC amplifier arranged to amplify AC components of a signal detected by the solid state detector.

46. The circular dichroism detection system according to claim 19, wherein the system is provided with a band pass filter tuned to the frequency of operation of the modulator means.

47. The circular dichroism detection system according to claim 45, wherein the system further comprises a multiplexor arranged to multiplex, for each detector of the array of solid state detectors, a DC signal and an AC signal after amplification.

48. The circular dichroism detection system according to claim 46, wherein synchronisation is performed by a fast programmable array.

49. The circular dichroism detection system according to claim 47, wherein the system further comprises a personal computer arranged to receive data, and to control operation of components of the system.

50. The circular dichroism detection system according to claim 48, wherein the array of solid state detectors is translatable and pivotable to allow it to be aligned with the beam.

51. The circular dichroism detection method according to claim 27, wherein the detected signals are digitised.

* * * * *